United States Patent
Nelson et al.

[11] Patent Number: 5,824,071
[45] Date of Patent: Oct. 20, 1998

[54] APPARATUS FOR TREATMENT OF ISCHEMIC HEART DISEASE BY PROVIDING TRANSVENOUS MYOCARDIAL PERFUSION

[75] Inventors: James A. Nelson, Seattle; Ascher Shmulewitz, Mercer Island, both of Wash.

[73] Assignee: Circulation, Inc., Menlo Park, Calif.

[21] Appl. No.: 798,700

[22] Filed: Feb. 12, 1997

Related U.S. Application Data

[62] Division of Ser. No. 714,466, Sep. 16, 1996, Pat. No. 5,655,548.
[51] Int. Cl.$^6$ .................................................. A61M 1/10
[52] U.S. Cl. ....................................... 623/3; 604/8
[58] Field of Search ............................ 128/898; 604/96, 604/49, 7–9, 93, 916; 606/194; 623/3, 1, 11, 900; 600/16

[56] References Cited

U.S. PATENT DOCUMENTS

| | | | |
|---|---|---|---|
| 4,302,854 | 12/1981 | Runge | 623/3 |
| 4,382,445 | 5/1983 | Sommers | 604/8 |
| 4,712,551 | 12/1987 | Rayhanabad | 604/8 X |
| 4,995,857 | 2/1991 | Arnold | 623/3 X |
| 5,287,861 | 2/1994 | Wilk . | |
| 5,352,240 | 10/1994 | Ross | 623/1 X |
| 5,380,316 | 1/1995 | Aita et al. . | |
| 5,389,096 | 2/1995 | Aita aet al. . | |
| 5,409,019 | 4/1995 | Wilk . | |
| 5,429,144 | 7/1995 | Wilk . | |
| 5,445,600 | 8/1995 | Abdulla | 604/9 |
| 5,456,714 | 10/1995 | Owen | 604/8 X |
| 5,549,581 | 8/1996 | Lurie et al. . | |
| 5,607,465 | 3/1997 | Camilli | 623/11 X |

FOREIGN PATENT DOCUMENTS

WO 97/13463  4/1997  WIPO .
WO 97/13471  4/1997  WIPO .

OTHER PUBLICATIONS

Mohl, Werner, "Coronary Sinus Interventions: From Concept to Clinics," *Journal of Cardiac Surgery*, vol. 2, No. 4, (Dec. 1987), pp. 467–493.

*Cardiac Catheterization and Angiography*, William Grossman, Ed., Lea & Febiger, Philadelphia (1980), pp. 63–69.

Ihnken, Kai et. al., "The Safety of Simultaneous Arterial and Coronary Sinus Perfusion: Experimental Background and Initial Clinical Results," *Journal of Cardiac Surgery*, vol. 9, No. 1, (Jan. 1994), pp. 15–25.

Ihnken, Kai et al., "Simultaneous Arterial and Coronary Sinus Cardioplegic Perfusion: an Experimental and Clinical Study," *The Thoracic and Cardiovascular Surgeon*, vol. 42, (Jun. 1994), pp. 141–147.

(List continued on next page.)

*Primary Examiner*—Mickey Yu
*Assistant Examiner*—Kelly O'Hara
*Attorney, Agent, or Firm*—Fish & Neave; Nicola A. Pisano

[57] ABSTRACT

Apparatus and methods are provided for use in open surgical and transluminal methods for supplying long-term retrograde perfusion of the myocardium via a conduit disposed between the left ventricle and the coronary sinus. In a first method, an opening is formed between the left ventricle and the coronary sinus, and the coronary ostium is partially occluded using a stent that prevents the pressure in the coronary sinus from exceeding a predetermined value. In an alternative method, a first end of a conduit is inserted transseptally through the right atrium and obliquely into the posterior septal endocardium of the left ventricle via the posterior pyramidal space, while a second end of the conduit is inserted into the coronary sinus via the coronary ostium. A pressure-limiting valve is included in the conduit. In either method, the outlet from the left ventricle to the coronary sinus may include a one-way valve to prevent backflow from the coronary sinus into the left ventricle during cardiac diastole.

22 Claims, 7 Drawing Sheets

OTHER PUBLICATIONS

Iguidbashian, John P. et al., "Advantages of Continuous Noncardioplegic Warm Blood Retrograde Perfusion over Antegrade Perfusion During Proximal Coronary Anastomoses," *Journal of Cardiac Surgery*, vol. 10, No. 1, (Jan. 1995), pp. 27–31.

Lichtenstein, Samuel V. et al., "Warm Retrograde Cardioplegia: Protection of the Right Ventrical in Mitral Valve Operations," *The Journal of Thoracic and Cardiovascular Surgery*, vol. 104, No. 2, (Aug. 1992), pp. 374–380.

Ropchan, Glorianne V. et al., "Salvage of Ischemic Myocardium by Nonsynchronized Retroperfusion in the Pig," *The Journal of Thoracic and Cardiovascular Surgery*, vol. 104, No. 3, (Sep. 1992), pp. 619–625.

Franz, N. et al., "Transfemoral Ballon Occlusion of the Coronary Sinus in Patients with Angina Pectoris," *Radiologia Diagnostica*, 31(1), (1990), pp. 35–41.

Kuraoka, S. et al., "Antegrade or Retrograde Blood Cardioplegic Method: Comparison of Postsurgical Right Ventricular Function and Conduction Disturbances," *Japanese Journal of Throacic Surgery*, 48(5), (May 1995), pp. 383–386.

Lincoff, A.M. et al., "Percutaneous Support Devices for High Risk or Complicated Coronary Angiopolasty," *Journal of the American College of Cardiology*, 17(3), (Mar. 1991), pp. 770–780.

Rudis, E. et al., "Coronary Sinus Ostial Occlusion During Retrograde Delivery of Cardioplegic Solution Significantly Improves Cardioplegic Distribution and Efficacy," *Journal of Thoracic and Cardiovascular Surgery*, 109(5), (May 1995), pp. 941–946.

Huang, A.H. et al., "Coronary Sinus Pressure and Arterial Venting Do Not Affect Retrograde Cardioplegia Distribution," *Annals of Thoracic Surgery*, 58(5), (Nov. 1994), pp. 1499–1504.

Tokunaga, S., et al., "Left Ventricular–Coronary Sinus Shunt Through a Septal Aneurysm After Mitral Valve Replacement," Annals of Thoracic Surgery, 59(1), (Jan. 1995), pp. 224–227.

Goldman, Alfred, M.D. et al., "Experimental Methods for Producing a Collateral Circulation to the Heart Directly from the Left Ventrical," *Journal of Thoracic Surgery*, Mar. 1956, pp. 364–347.

Massimo, C., M.D. et al., "Myocardial Revascularization by a New Method of Carrying Blood Directly from the Left Ventricular Cavity into the Coronary Circulation," *Journal of Thoracic Surgery*, Aug. 1957, pp. 257–264.

Munro, Ian, M.B. et al., "The Possibility of Myocardial Revascularization by Creation of a Left Ventriculocoronary Artery Fistula," *Journal of Thoracic and Cardiovascular Surgery*, vol. 58, No. 1, Jul. 1969, pp. 25–32.

APPARATUS FOR TREATMENT OF ISCHEMIC HEART DISEASE BY PROVIDING TRANSVENOUS MYOCARDIAL PERFUSION

This application is a division of U.S. Pat. No. 08/714,466, filed Sep. 16, 1996 now U.S. Pat. No. 5,655,548, entilted METHOD AND APPARATUS FOR TREATMENT OF ISCHEMIC HEART DISEASE BY PROVIDING TRANSVENOUS MYOCARDIAL PERFUSION.

FIELD OF THE INVENTION

The present invention relates generally to treatment of ischemic heart disease, and more particularly, cases involving diffuse coronary atherosclerosis, by perfusing the myocardium with oxygenated blood from the left ventricle using the venous system of the heart.

BACKGROUND OF THE INVENTION

The cardiac blood perfusion system is composed of two coronary arterial vessels, the left and right coronary arteries, which perfuse the myocardium from the epicardial surface inward towards the endocardium. Blood flows through the capillary systems into the coronary veins, and into the right atrium via the coronary sinus. Two additional systems, the lymphatic and the Thebesian veins, drain a portion of the blood perfused into the myocardium directly into the heart chambers. The venous system has extensive collaterals and, unlike the coronary arteries, does not occlude in atherosclerotic disease.

A number of techniques have been developed to treat ischemic heart disease caused, for example, by atherosclerosis. These treatments have improved the lives of millions of patients worldwide, yet for certain classes of patients current technology offers little hope or relief.

Best known of the current techniques is coronary artery bypass grafting, wherein a thoracotomy is performed to expose the patient's heart, and one or more coronary arteries are replaced with synthetic grafts. In preparation for the bypass grafting, the heart is arrested using a suitable cardioplegia solution, while the patient is placed on cardiopulmonary bypass (i.e., a heart-lung machine) to maintain circulation throughout the body during the operation. Typically, a state of hypothermia is induced in the heart muscle during the bypass operation to reduce oxygen utilization, thereby preserving the tissue from further necrosis. Alternatively, the heart may be perfused throughout the operation using either normal or retrograde flow through the coronary sinus, with or without hypothermia. Once the bypass grafts are implanted, the heart is resuscitated, and the patient is removed from cardiopulmonary bypass.

Drawbacks of conventional open heart surgery are that such surgery is time-consuming and costly, involves a significant risk of mortality, requires a lengthy period of recuperation, and involves significant discomfort to the patient.

As a result of the foregoing drawbacks, techniques have been developed that permit coronary bypass grafting to be performed endoscopically, i.e., using elongated instruments inserted through incisions located between the ribs. A drawback of these keyhole techniques, however, is that they can be used only for coronary arteries that are readily accessible, and not, for example, those located posteriorly.

Alternatively, techniques such as percutaneous transluminal angioplasty ("PTA") have been developed for reopening arteries, such as the coronary arteries, that have become constricted by plaque. In these techniques, a balloon catheter is typically inserted into the stenosis and then inflated to compress and crack the plaque lining the vessel, thereby restoring patency to the vessel. Additionally, a vascular prosthesis, commonly referred to as a "stent," may be inserted transluminally and expanded within the vessel after the angioplasty procedure, to maintain the patency of the vessel after the PTA procedure.

U.S. Pat. No. 5,409,019 to Wilk describes an alternative method of creating a coronary bypass, wherein a valve-like stent is implanted within an opening formed between a coronary artery and the left ventricle. The patent describes that the stent may be implanted transluminally.

A drawback of the foregoing transluminal approaches is that the treatment device, e.g., the balloon catheter or the stent delivery system described in U.S. Pat. No. 5,409,019, must be inserted in the vessel before it can be expanded. Occasionally, a stenosis may occlude so much of a vessel that there is insufficient clearance to advance a guidewire and catheter within the stenosis to permit treatment. In addition, arterial blockages treatable using PTA techniques are restricted to the portions of the anatomy where such techniques can be beneficially employed.

Moreover, the above-described techniques—both open-surgery and transluminal—are useful only where the stenosis is localized, so that the bypass graft or PTA procedure, when completed, will restore near normal blood flow to the effected areas. For certain conditions, however, such as diffuse atherosclerosis, blockages may exist throughout much of the coronary artery system. In such situations, treatment, if possible, typically involves heart transplant.

Historically, attempts have been made to treat diffuse blockages of the coronary arterial system by introducing retrograde flow through the coronary venous system. As described,. for example, in W. Mohl, "Coronary Sinus Interventions: From Concept to Clinics," *J. Cardiac Surg.*, Vol. 2, pp. 467–493 (1987), coronary venous bypass grafts have been attempted wherein the coronary sinus was ligated, and a shunt was implanted between a cardiac vein and the aorta, thus providing permanent retrograde perfusion. It was observed that such bypass grafts resulted in underperfusion of certain regions of the myocardium and edema of the venous system. Consequently, as reported in the aforementioned Mohl article, these techniques are rarely used in cardiac surgery, while permanent retroperfusion is never used in interventional cardiology.

Despite disenchantment with retroperfusion via the coronary sinus for long-term perfusion of the myocardium, retrograde coronary venous perfusion is now routinely used in coronary interventional procedures to perfuse the heart during the procedure. Franz et al., in "Transfemoral Balloon Occlusion of the Coronary Sinus in Patients with Angina Pectoris,"*Radiologia Diagnostica*, 31(1), pp. 35–41 (1990), demonstrated the possibility of transfemoral coronary sinus balloon occlusion in patients with angina pectoris. In recent years, the use of retrograde arterial perfusion of blood through the coronary sinus has gained wide acceptance as a technique to preserve the myocardium during bypass procedures (Kuraoka et al., "Antegrade or Retrograde Blood Cardioplegic Method: Comparison of Post-Surgical Right Ventricular Function and Conduction Disturbances," *Japanese J. Thoracic Surg.*, 48(5), pp. 383–6, (1995)) and during high risk or complicated angioplasty (Lincoff et al., "Percutaneous Support Devices for High Risk or Complicated Coronary Angioplasty," *J. Am. Coll. Cardiol.*, 17(3), pp.

770–780 (1991)). This perfusion technique allows continuous warm cardioplegia and allows the flow of blood through the coronary venous bed distal to the occlusion.

It has also been reported by Rudis et al. in "Coronary Sinus Ostial Occlusion During Retrograde Delivery of Cardioplegic Solution Significantly Improves Cardioplegic Distribution and Efficiency," *J. Thoracic & Cardiovasc. Surg.*, 109(5), pp. 941–946 (1995), that retrograde blood flow through the coronary venous system may be augmented by coronary ostial occlusion. In this case, blood flows retrograde to the myocardium and drainage is through the lymphatic system and the Thebesian veins. Huang et al., in "Coronary Sinus Pressure and Arterial Venting Do Not Affect Retrograde Cardioplegic Distribution," *Annals Thoracic Surg.*, 58(5), pp. 1499–1504, that flow through the myocardium is not significantly effected by coronary arterial occlusion and venting, or by increases in coronary perfusion pressure. Also, K. Ihnken et al., in "Simultaneous Arterial and Coronary Sinus Cardioplegic Perfusion, an Experimental and Clinical Study," *Thoracic and Cardiovascular Surgeon*, Vol. 42, pp. 141–147 (June 1994), demonstrated the benefits of using simultaneous arterial and coronary sinus perfusion during cardiac bypass surgery, with no ventricular edema, lactate production, lipid peroxidation, or effect on post-bypass left ventricular elastance or stroke work index.

For a large number of patients in the later phases of ischemic heart disease, and particularly diffuse atherosclerotic disease, current technology offers little relief or hope. In such instances, humanely extending the patient's life for additional months may provide significant physical and emotional benefits for the patient.

In view of the foregoing, it would be desirable to provide methods and apparatus for use in treating ischemic heart disease in a wider range of open surgical and interventional cardiology procedures.

It also would be desirable to provide methods and apparatus for providing transvenous myocardial perfusion that reduce the risk of edema within the venous system.

It would further be desirable to provide methods and apparatus that enable patients suffering from the later phases of diffuse ischemic heart disease to experience renewed vigor, reduced pain and improved emotional well-being during the final months or years of their lives.

SUMMARY OF THE INVENTION

In view of the foregoing, it is an object of this invention to provide methods and apparatus for use in treating ischemic heart disease in a wider range of open surgical and interventional cardiology procedures.

It is another object of the present invention to provide methods and apparatus for providing transvenous myocardial perfusion that reduce the risk of edema within the venous system.

It is a further object of this invention to provide methods and apparatus that enable patients suffering from the later phases of diffuse ischemic heart disease to experience renewed vigor, reduced pain and improved emotional well-being during the final months or years of their lives.

In accordance with the present invention, open surgical and transluminal methods are provided for supplying long-term retrograde perfusion of the myocardium via a conduit disposed between the left ventricle and the coronary sinus.

In a first method performed in accordance with the present invention, apparatus for forming an opening between the coronary sinus and the left ventricle is advanced into the coronary sinus through the coronary ostium (located in right atrium). Access to the right atrium may be established using either the subclavian veins and the superior vena cava or an approach through a femoral vein. Once an opening is formed between the left ventricle and the coronary sinus, the coronary ostium is partially occluded using a stent that prevents pressure in the coronary sinus from exceeding a predetermined value, generally, about 60 mm Hg. Optionally, a valved stent may be disposed in the passageway between the left ventricle and the coronary sinus to maintain the patency of the opening during cardiac systole and to prevent flow from the coronary sinus into the left ventricle during cardiac diastole.

In an alternative method of the present invention, suitable for use either as an open surgical procedure or as a transluminal procedure, a first end of a conduit is inserted transeptally through the right atrium and obliquely into the posterior septal endocardium of the left ventricle via the posterior pyramidal space, while a second end of the conduit is inserted into the coronary sinus via the coronary ostium in the right atrium. As in the first method, the conduit may include means for maintaining pressure in the conduit and coronary sinus below a predetermined value, and may include a one-way valve preventing backflow from the coronary sinus to the left ventricle during cardiac diastole.

Further features of the invention, its nature and various advantages will be more apparent from the accompanying drawings and the following detailed description of the preferred embodiments.

BRIEF DESCRIPTION OF THE DRAWINGS

FIGS. 8A, 8B, 8D and 8E are sectional views of a human heart illustrating the steps of transluminally creating a venous bypass in accordance with the principles of the present invention, while

DETAILED DESCRIPTION OF THE INVENTION

The present invention relates generally to methods and apparatus for providing transvenous myocardial perfusion for patients suffering from diffuse forms of ischemic heart disease, such as atherosclerosis. In accordance with the methods of the present invention, a conduit is formed between the left ventricle and the coronary sinus, so that blood ejected from the left ventricle enters the coronary sinus during cardiac systole. The apparatus of the present invention includes means for limiting peak pressure in the coronary sinus during cardiac systole to a value less than that believed to result in edema of the venous system, generally, about 60 mm Hg.

Figure 1:
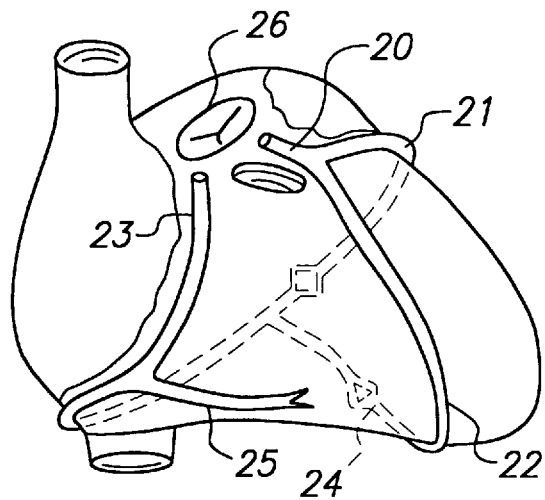
FIG. 1 is a partial perspective view of a human heart illustrating the coronary arteries.
Figure 2:
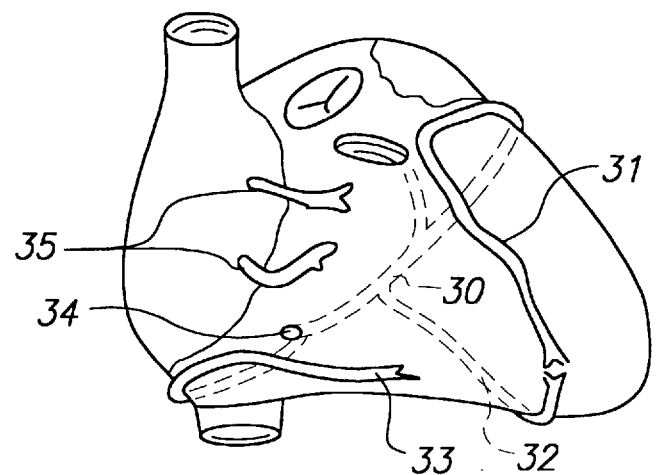
FIG. 2 is a partial perspective view of a human heart illustrating the cardiac veins.
Figure 3:
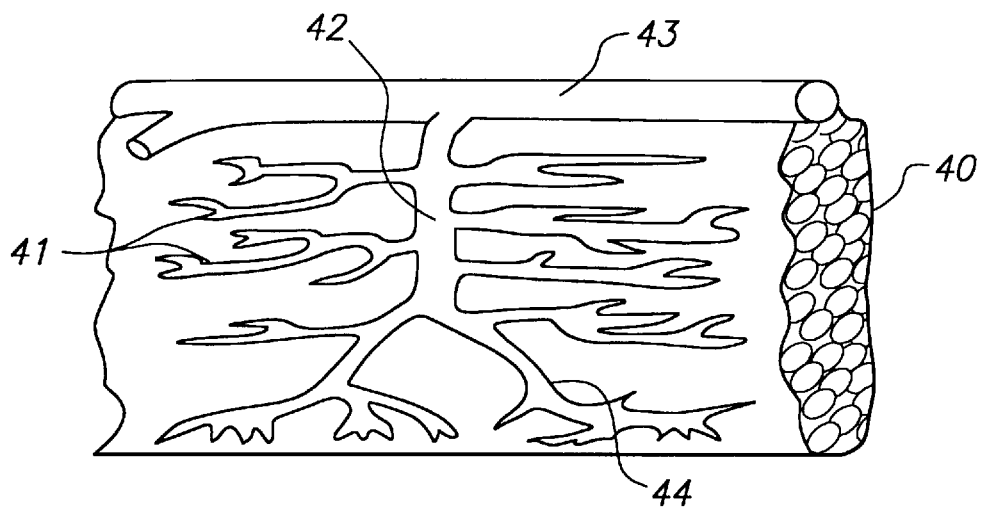
FIG. 3 is a sectional view of the myocardium, showing certain components of the cardiac venous system.

Referring to FIGS. 1 to 3, the coronary arterial and venous systems of the human heart are described. As shown in FIG. 1, the myocardium of a healthy human heart is nourished by left coronary artery 20, including circumflex branch 21 and anterior descending branch 22, and right coronary artery 23, including descending posterior branch 24 and marginal branch 25. Left and right coronary arteries 20 and 23 emanate from the aorta (not shown) slightly above aortic semilunar valve 26. During cardiac bypass surgery, it is common for occluded sections of the left and right coronary arteries 20 and 23 to be excised and replaced with synthetic grafts.

FIGS. 2 and 3 illustrate the cardiac venous system of the human heart and a model of the myocardial veins, respectively. The venous system comprises coronary sinus 30 that provides drainage for great cardiac vein 31, middle cardiac vein 32, and small cardiac vein 33. Deoxygenated blood flowing into coronary sinus 30 exits via coronary ostium 34 into the right atrium. The venous system further includes anterior cardiac veins 35 that drain directly into the right atrium.

With respect to FIG. 3, myocardium 40 includes a lattice of capillaries 41 that drain deoxygenated blood into intramyocardial veins 42. From myocardial veins 42, a fraction of the blood drains into the cardiac veins via subepicardial veins 43, while the remainder drains through the Thebesian veins 44 directly into the atrial and ventricular cavities. It has been reported in healthy human hearts that approximately 70% of the deoxygenated blood is drained through the coronary sinus, while the remaining 30% is drained in about equal proportions into the left and right atria and ventricles via the lymphatic system and the Thebesian veins. It has likewise been reported that when individual components of the venous system (i.e., the coronary sinus, lymphatic system and Thebesian veins) are occluded, the flow redistributes itself through the remaining unoccluded channels.

The coronary arteries are formed of resilient tissue fibers that withstand the peak pressures typically generated in the left ventricle during cardiac systole, generally up to about 120 mm Hg. By contrast, the tissue fibers of the cardiac veins are much less resilient than those of the coronary arterial system, with peak pressures in the coronary sinus generally in a range of 6–10 mm Hg. Consequently, as reported for example in the aforementioned Mohl article, adequate drainage of deoxygenated blood can be provided by the lymphatic system and the Thebesian veins even when the coronary sinus is totally occluded. However, as also reported in that article, long-term retroperfusion via the coronary sinus often leads to edema of the cardiac veins, which are generally believed to be incapable of sustaining long-term pressures above about 60 mm Hg. The methods and apparatus of the present invention are intended to address this significant drawback of long-term retroperfusion via the coronary sinus.

Figure 4:
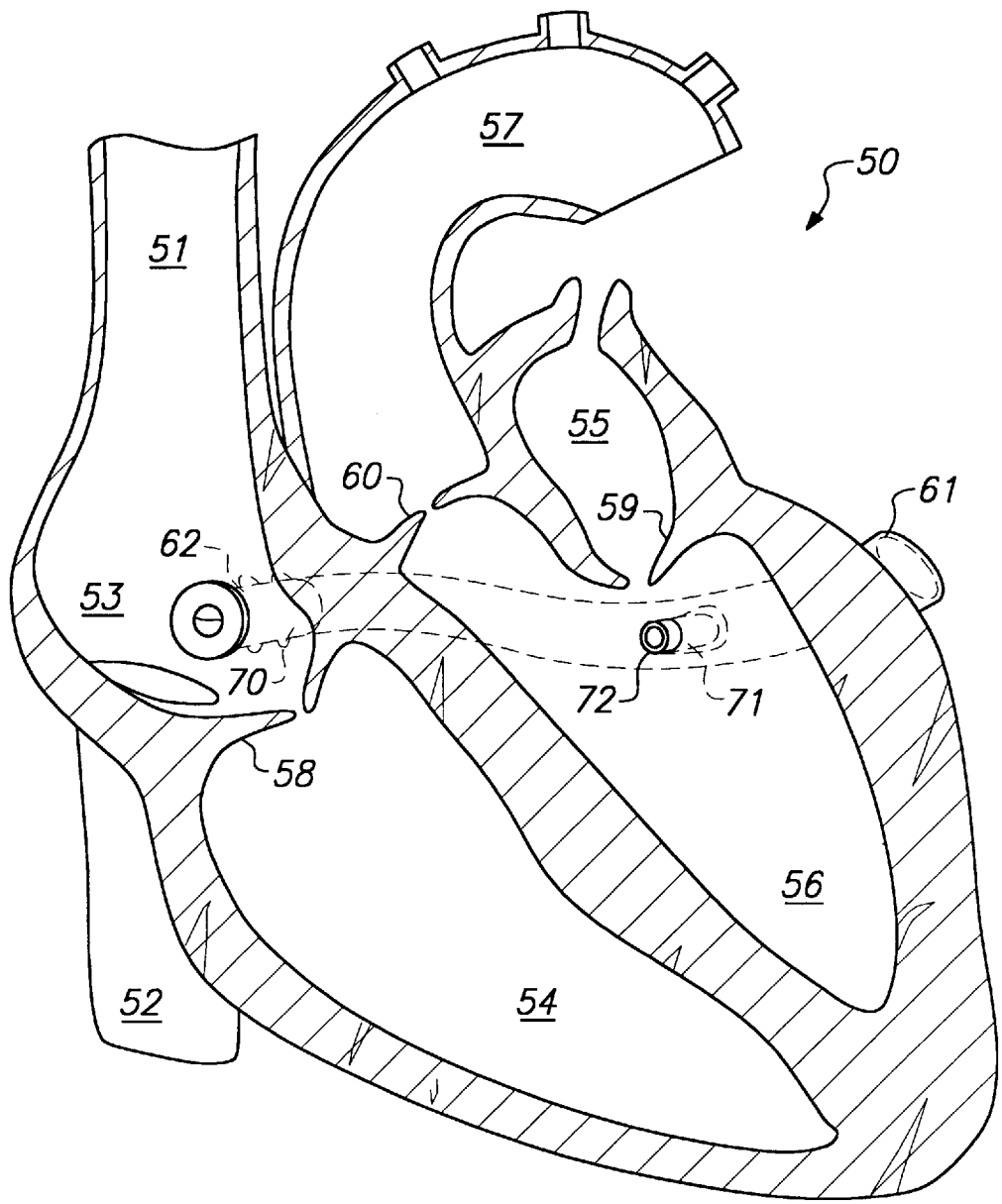
FIG. 4 is a sectional view of a human heart showing the placement of apparatus of the present invention in accordance with a first method of the present invention.

Referring now to FIG. 4, a first embodiment of the method and apparatus in accordance with the present invention is described. FIG. 4 depicts human heart 50 in cross-section, within which apparatus of the present invention has been implanted in accordance with the methods of the present invention. Human heart 50 includes superior vena cava 51 and inferior vena cava 52 communicating with right atrium 53, right ventricle 54, left atrium 55, left ventricle 56, and aorta 57 (for clarity, the pulmonary artery has been omitted). Tricuspid valve 58 separates right atrium 53 from right ventricle 54, while mitral valve 59 separates left atrium 55 from left ventricle 56. Aortic semilunar valve 60 separates left ventricle 56 from aorta 57. Coronary sinus 61 is shown in dotted outline passing behind heart 50 and exiting into right atrium 53 at coronary ostium 62.

Figure 5:
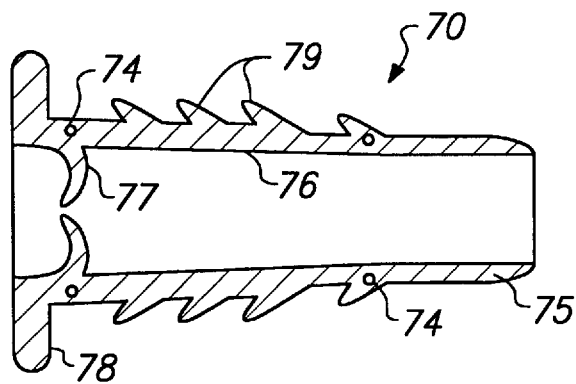
FIG. 5 is a sectional view of a plug constructed in accordance with the principles of the present invention for partially occluding the coronary ostium.

In accordance with a first method of the present invention, plug 70 is lodged in coronary ostium 62, while stent 71 is disposed in passageway 72 created between coronary sinus 61 and left ventricle 56. Plug 70, shown in greater detail in FIG. 5, preferably comprises a resilient biocompatible material, e.g., silicon or soft plastic, which is formed into a slightly tapered tubular member 75. Tubular member 75 includes bore 76 and pressure sensitive valve 77 disposed in bore 76. Tubular member 75 further includes proximal flange 78 that abuts against the right atrial endocardium and a plurality of resilient barbs or ribs 79 that engage the interior wall of the coronary sinus when plug 70 is disposed in the coronary sinus through coronary ostium 62, thereby securing plug 70 in position. Plug 70 also may include radiopaque marker rings 74, e.g., gold hoops, embedded in the thickness of tubular member 75 for determining the location and orientation of plug 70 under fluoroscopic imaging.

Pressure sensitive valve 77 is designed to remain closed until the pressure in the coronary sinus reaches about 60 mm Hg. Once the coronary sinus pressure reaches about 60 mm Hg, valve 77 opens to vent any additional blood ejected into the coronary sinus via passageway 72 and stent 71 into right atrium 53. Pressure sensitive valve 77 may be constructed employing knowledge per se known in the art for construction of synthetic valves such as the mitral, aortic, and pulmonary valves.

Figure 6:
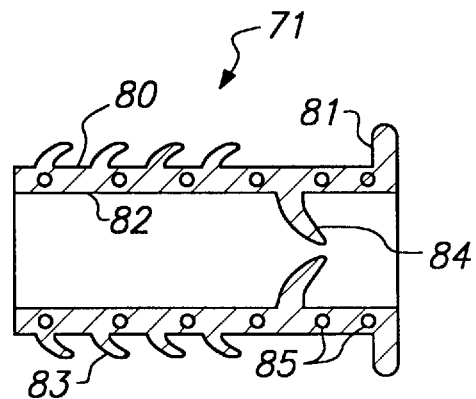
FIG. 6 is a sectional view of a stent constructed in accordance with the principles of the present invention for forming a conduit between the left ventricle and the coronary sinus, illustratively including a one-way valve.

Stent 71, shown in greater detail in FIG. 6, is preferably similar in design to plug 70, and includes a tubular member 80 having proximal flange 81, bore 82 and resilient barbs or ribs 83 disposed around its circumference. Stent 71 preferably comprises a compliant material capable of bending along its length, such as silicon or a resilient plastic, thus permitting the stent to be transported transluminally through tortuous passages. Stent 71 also may have embedded within tubular member 80 circumferential hoops 85 formed of a relatively rigid material, e.g., stainless steel. Hoops 85, if provided, enable the stent to resist radial compression, thereby enabling stent 71 to maintain the patency of bore 82 against contraction of the left ventricular myocardium during cardiac systole. Stent 71 optionally may include one-way valve 84 that prevents blood from being drawn from the coronary sinus into the left ventricle during cardiac diastole. Certain of hoops 85 also may be coated with a radiopaque material visible under fluoroscopic imaging.

Proximal flange 81 abuts against the interior wall of the coronary sinus when stent 71 is implanted in passageway 72 formed between the coronary sinus and the myocardium of the left ventricle. When stent 71 is positioned in passageway 72 as shown in FIG. 4, barbs or ribs 83 secure stent 71 from withdrawing into the coronary sinus, while proximal flange 81 prevents the stent from being drawn into the left ventricle.

Figure 7:
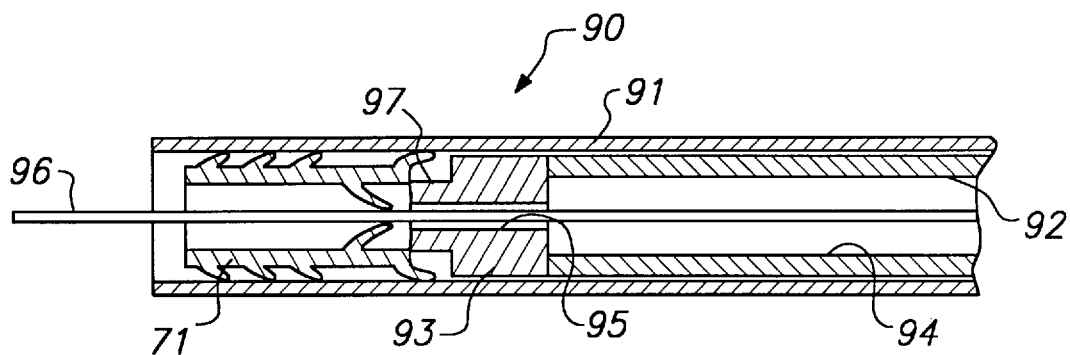
FIG. 7 is a sectional view of the distal end of a catheter system constructed in accordance with the principles of the present invention for delivering the plug and stent of FIGS. 5 and 6.

Plug 70 and stent 71 are transported to, and implanted within, the coronary sinus using flexible catheter 90, the distal end of which is shown in FIG. 7. In one embodiment of the present invention, catheter 90 includes exterior sheath 91, pusher member 92 disposed to reciprocate within exterior sheath 92 and spool 93 affixed to the distal end of pusher member 92. Pusher member 92 and spool 93 include central bores 94 and 95, respectively, through which guidewire 96 slidably extends. The distal end of spool 93 includes step 97 that is dimensioned to loosely engage bore 82 of stent 71 (as well as bore 76 of plug 70). Stent 71 is loaded into the distal end of catheter 90 within exterior sheath 91 so that flange 81 of the stent is flexibly bent longitudinally between spool 93 and exterior sheath 91, and step 97 engages the proximal end of bore 82. Guidewire 96 extends through one-way valve 84 (if provided).

Figure 8A:
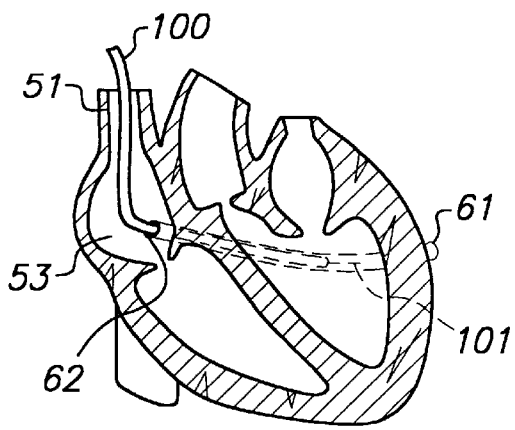

Implantation of apparatus 70 in accordance with a first method of the present invention is now described with respect to FIGS. 8A through 8E. In FIG. 8A, catheter 100 is advanced along guidewire 101 through the axillary and subclavian veins (not shown) and into right atrium 53 via superior vena cava 51. Catheter 100 is then advanced through coronary ostium 62 and into coronary sinus 61. Catheter 100 preferably includes piezoelectric ultrasound elements for mapping the coronary sinus, the left ventricular myocardium, and the anatomy of the left ventricle.

Figure 8B:
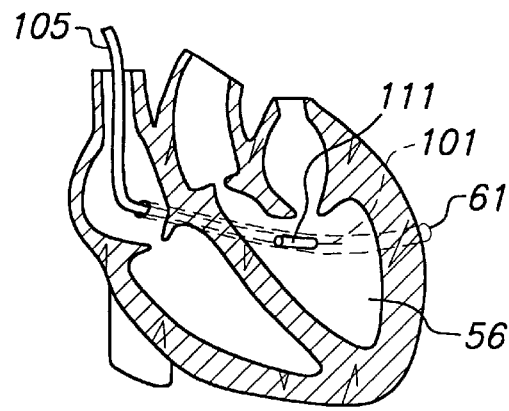
Figure 8C:
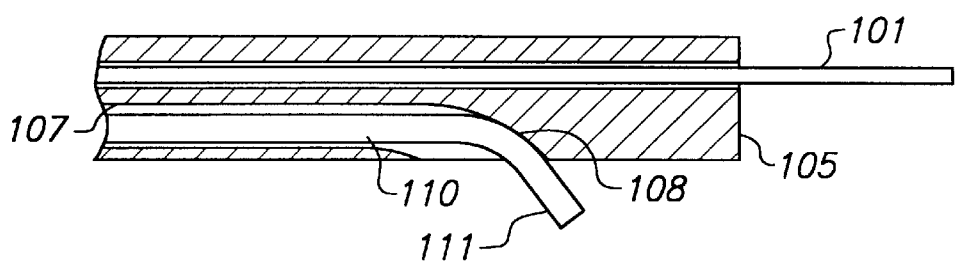
FIG. 8C is a cross-sectional view of a catheter suitable for use with a cutting instrument for forming a passageway from the coronary sinus to the left ventricle.

Once the cardiologist has mapped these features of the heart, catheter 100 is withdrawn (guidewire 101 is left in place) and catheter 105 is advanced along guidewire and into the coronary sinus. The distal end of catheter 105 is illustrated in FIG. 8C as including lumen 106 through which guidewire 101 is slidably disposed, and lumen 107 which exits through a lateral face of catheter 105 at radiused skive 108. Cutting instrument 110 is advanced through lumen 107 so that its distal end extends from skive 108 and is substantially transverse to the longitudinal orientation of catheter 105.

Cutting instrument 110 includes an end effector at its distal end 111 which is capable of penetrating the wall of coronary sinus 61 and left ventricle 56 to form passageway 72 therebetween. Cutting instrument may comprise, for example, a medical laser, as described, for example, in U.S. Pat. No. 5,104,393, which is incorporated herein by reference, or a mechanical cutting element, such as a rotating blade (commonly used in atherectomy), or a cannulating needle. As shown in FIG. 8B, once distal end 111 of cutting instrument 110 is advanced into the left ventricle, the cutting instrument is withdrawn from lumen 107 while catheter 105 is retained in place.

Figure 8D:
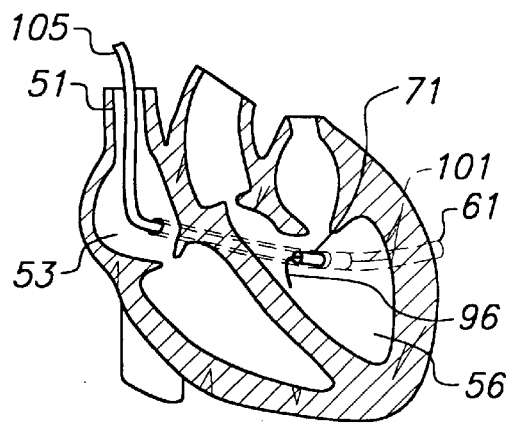

Referring now to FIGS. 7 and 8D, guidewire 96 and catheter 90 (carrying stent 71) are advanced through lumen 107 of catheter 105 until guidewire 96 enters through passageway 72 into left ventricle 56. Catheter 90 is advanced along guidewire 96 until it abuts the wall of the coronary sinus. Pusher member 94 is then advanced within exterior sheath 91 so that spool 93 urges stent 71 out of sheath 91 and, guided by guidewire 96, into engagement in passageway 72. When implanted, flange 81 contacts the interior wall of the coronary sinus while tubular member 80 extends into the myocardium of the left ventricle, with barbs or ribs 83 anchoring stent 71 in position. Catheter 90, guidewire 96 and catheter 105 are then withdrawn from the coronary sinus via the coronary ostium, while guidewire 101 remains in place.

Figure 8E:
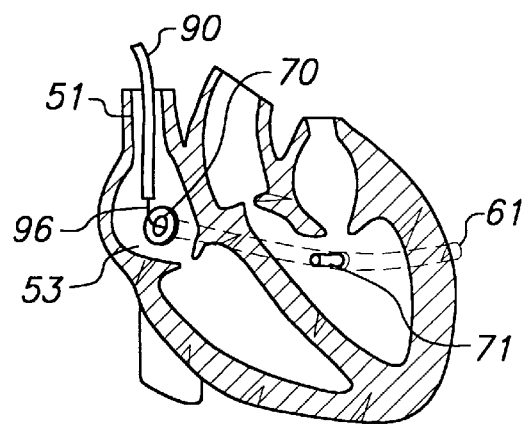

In FIG. 8E, a new catheter 90 loaded with plug 70 is advanced along guidewire 101 so that the tapered end of plug 70 enters through the coronary ostium and engages the interior wall of the coronary sinus. Pusher member 94 is again advanced to implant plug 70 into the coronary sinus through the coronary ostium, so that flange 78 of plug 70 contacts the endocardium of right atrium 53. Guidewire 101 and catheter 90 are then withdrawn, completing the procedure.

Applicants expect that when implanted in the heart, plug 70 and stent 71 will result in long-term retrograde perfusion of the myocardium using the cardiac venous system, and will cause a redistribution of flow within the venous system so that a greater fraction of the deoxygenated blood exits via the lymphatic system and the Thebesian veins. And because valve 77 of plug 70 opens when the pressure in the coronary sinus exceeds about 60 mm Hg, it is expected that problems associated with edema of the cardiac veins observed in the aforementioned historical attempts at coronary venous bypass grafting will be overcome. Applicants further note that while the venous system is not co-extensive with the coronary arteries (particularly with respect to the right ventricle), it is nevertheless expected that the method and apparatus of the present invention will provide relief in the majority of cases, since right ventricular infarcts are less common.

As will be apparent to one of skill in the art of cardiology, the above described methods may be practiced with other instruments and techniques which are per se known. For example, conventional angiographic methods may be employed to map the arterial and venous systems and the anatomy of the left ventricle. In addition, access to the coronary sinus may be had via the femoral veins. Moreover, passageway 72 could be created between the left ventricle and the coronary sinus by advancing the cutting instrument from within the left ventricle (for example, by insertion through a femoral artery, the aorta, and through the aortic valve) and into the coronary sinus, after which stent 71 could be disposed in the passageway with flange 81 engaging the left ventricular endocardium.

Figure 9:
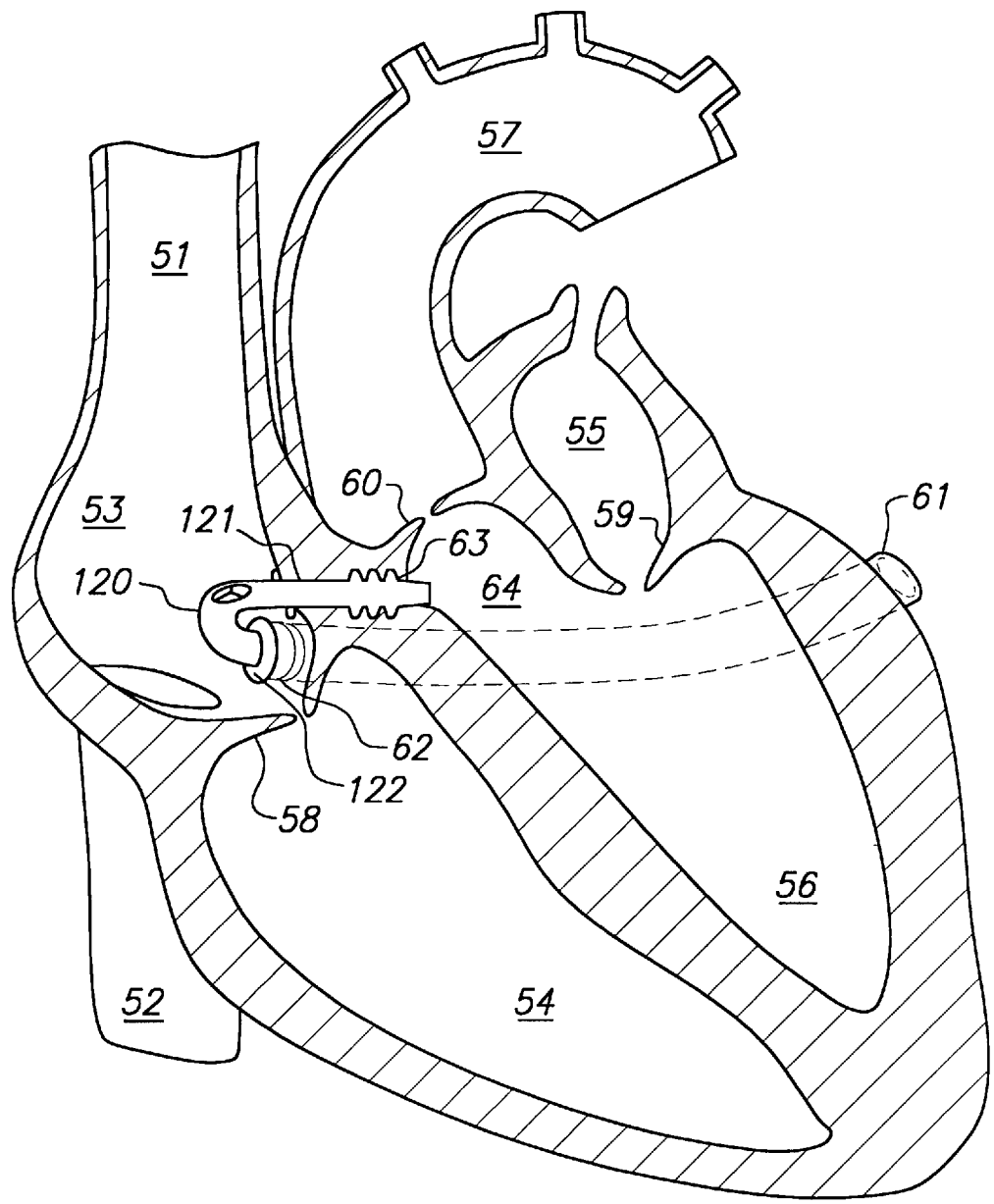
FIG. 9 is a sectional view of a human heart showing the placement of alternative apparatus of the present invention in accordance with an alternative method of the present invention.

Referring now to FIG. 9, an alternative method of creating a venous bypass is described, in which like parts of the heart are labeled with like reference numerals. In FIG. 9, first end 121 of conduit 120 is placed in passageway 63 created between right atrium 53 and posterior septal endocardium 64 of left ventricle 56, while second end 122 of conduit 120 extends through coronary ostium 62 and engages the interior wall of coronary sinus 61.

Figure 10:
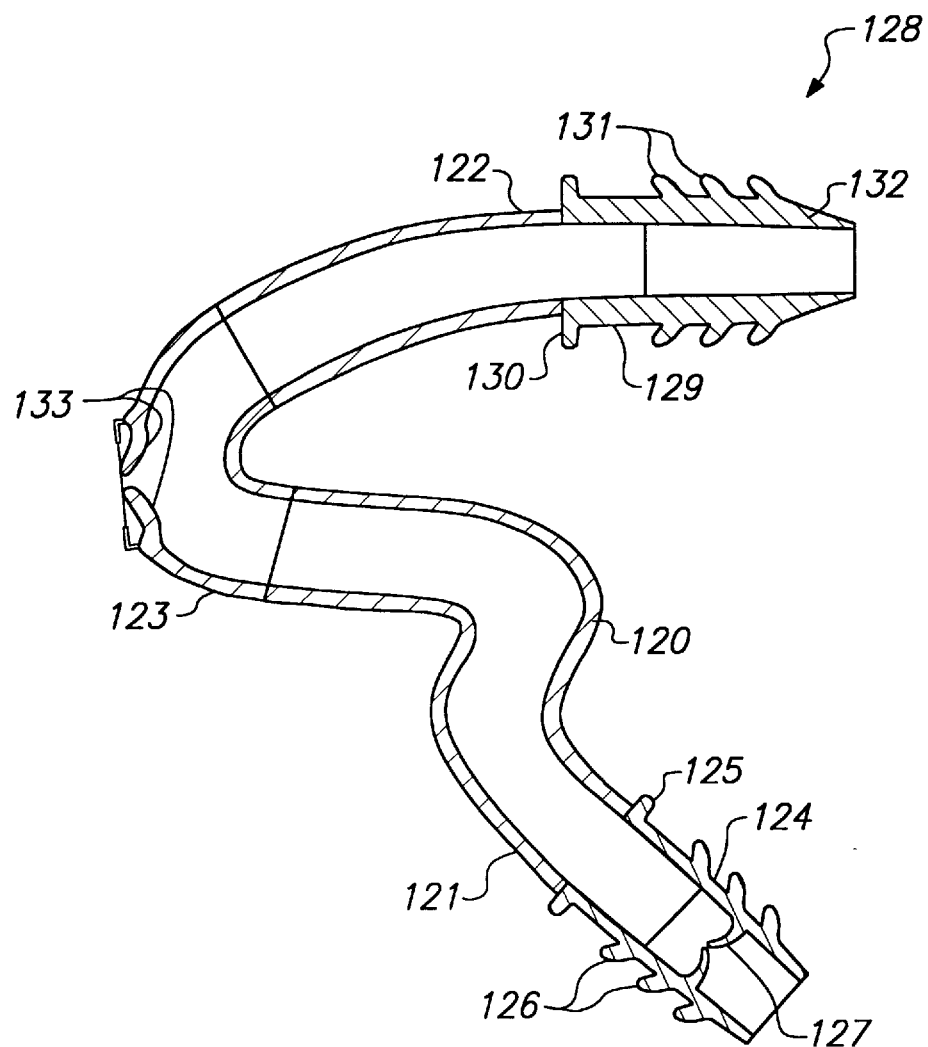
FIG. 10 is a sectional view of alternative apparatus constructed in accordance with the principles of the present invention for forming a conduit between the left ventricle and the coronary sinus, illustratively including a one-way valve adjacent the inlet from the left ventricle.

Conduit 120, shown in FIG. 10, has first end 121, second end 122 and valved section 123. Conduit 120 may be formed of a flexible and compliant material, such as silicon tubing, or a suitable synthetic graft material, for example, a polyester fabric, such as Dacron®, a registered trademark of E.

I. DuPont de Nemours, Wilmington, Del. The material selected for conduit 120 may vary depending upon the intended method of implantation of the conduit. For example, if conduit 120 is to be implanted surgically, there may be advantages to employing a material such as silicon tubing for the conduit. Alternatively, if conduit 120 is to be implanted transluminally, it may be advantageous to employ a material such as a biocompatible fabric that can be compressed to a smaller diameter to pass through a catheter.

First end 121 of conduit 120 has disposed from it tubular member 124 similar in construction to stent 71 of FIG. 6. Tubular member 124, which may comprise a compliant material as described hereinabove with respect to stent 71, includes proximal flange 125 and a plurality of ribs or barbs 126 that engage the myocardium and prevent movement of first end 121 when it is implanted. Tubular member 124 may optionally include one-way valve 127 to prevent suction of blood from conduit 120 into the left ventricle during cardiac diastole.

Second end 122 of conduit 120 includes fitting 128. Fitting 128 comprises tubular member 129 having proximal flange 130, a plurality of outwardly extending barbs or ribs 131, and tapered distal portion 132. When implanted in the heart, tapered portion 132 of fitting 128 extends through the coronary ostium into the coronary sinus, while flange 130 abuts against the right atrial endocardium.

Still referring to FIG. 10, conduit 120 includes valved section 123, which may be disposed between first and second ends 121 and 122 of conduit 120, so as to not interfere with implantation of either tubular member 124 or fitting 128. Valved section 123 includes pressure sensitive valve 133 disposed in its lateral wall. Valve 133 serves the same function in the present embodiment as valve 77 serves in the embodiment of FIG. 5. In particular, valve 133 is constructed to open when the pressure in conduit 120 exceeds a predetermined value, for example, 60 mm Hg.

As will be apparent from the design of conduit 120 and the description hereinabove, conduit 120 provides retroperfusion of the myocardium via the coronary sinus when implanted. During cardiac systole, blood in the left ventricle is pushed through tubular member 124, through conduit 120, and into coronary sinus 61 via fitting 128. When the pressure exceeds the peak pressure sustainable by the coronary sinus, valve 133 opens to vent blood from the left ventricle into the right atrium, thereby preventing further rise in the pressure induced in the coronary sinus. Applicants expect that this aspect of the present invention will provide improved myocardium perfusion without the problems encountered in earlier attempts to provide transvenous myocardial perfusion.

Conduit 120 of FIGS. 9 and 10 may be surgically implanted in the heart using a variation of conventional surgical technique. In particular, following a conventional thorocotomy to expose the heart, an incision may be made through the exterior wall of the right atrium. A passageway is formed between right atrium 53 and the posterior septal endocardium 64 of the left ventricle via the posterior pyramidal space using a cannulating needle. Tubular member 124 is then implanted in the passageway. Second end 122 of conduit is implanted in coronary ostium 62 so that tapered end 132 extends into the coronary sinus and flange 130 abuts against the right atrial endocardium.

Alternatively, conduit 120 may be implanted using a transluminal approach that is a variation of the Brockenbrough method of catheterizing the left ventricle. The conventional Brockenbrough technique is described in CARDIAC CATHETERIZATION AND ANGIOGRAPHY, W. Grossman, ed., at pages 63–69, published by Lea & Febiger, Philadelphia (1980), which is incorporated herein by reference. In the conventional Brockenbrough technique, a catheter and needle combination is advanced through the right femoral artery and into the right atrium. The needle is then used to puncture the septum between the right and left atria, after which the catheter is advanced through the mitral valve and into the left ventricle.

In accordance with the present invention, a Brockenbrough needle kit, available from United States Catheter and Instrument Corp., Billerica, Mass., is advanced over a guidewire into the right atrium via the right internal jugular vein using standard Seldinger technique. The Brockenbrough needle is then advanced through the right atrial endocardium, the posterior pyramidal space, and through the septal endocardium of the left ventricle to form a passageway between the right atrium and the septal endocardium of the left ventricle. The initial transeptal puncture made with the Brockenbrough needle is dilated using, for example, progressively larger catheters, which are then withdrawn, leaving the guidewire in place.

Figure 11A:
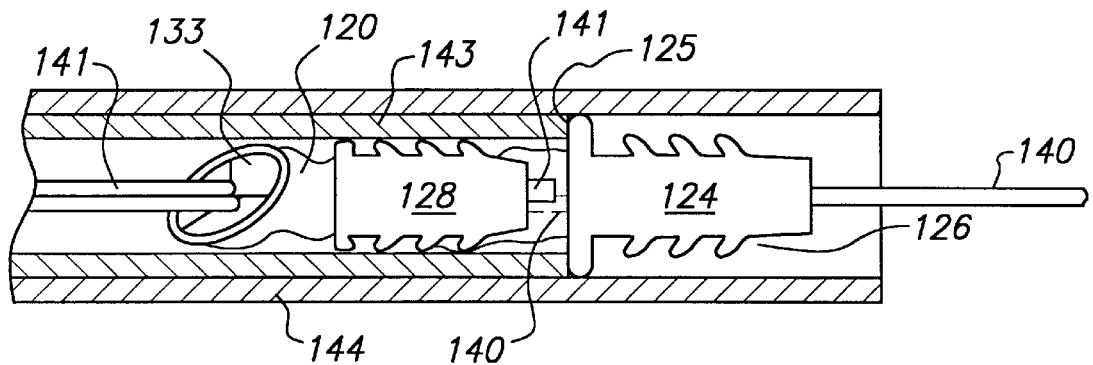
FIGS. 11A and 11B are, respectively, an illustrative sectional view of apparatus for implanting a first end of the conduit constructed in accordance with the present invention, and a perspective view of a step of transluminally implanting the apparatus of FIG. 10.

Referring now to FIG. 11A, conduit 120 is threaded onto the proximal end of guidewire 140 that is positioned in the transeptal passageway. Conduit 120 is placed on guidewire 140 so that the guidewire enters the conduit through valve 133 and extends through tubular member 124. Conduit 120 is folded over so that second guidewire 141 extends through valve 133 and fitting 128. Pusher member 143 is disposed around conduit 120 so that it contacts the proximal face of flange 125, the remainder of conduit 120, including fitting 128 and valved section 123, being inserted within a lumen of pusher member 143. Pusher member 143 and conduit 120 are then loaded into exterior sheath 144. Using this arrangement, pusher member 143 is disposed to push tubular member 124 (and connected conduit 120) in a distal direction along guidewire 140.

Figure 11B:
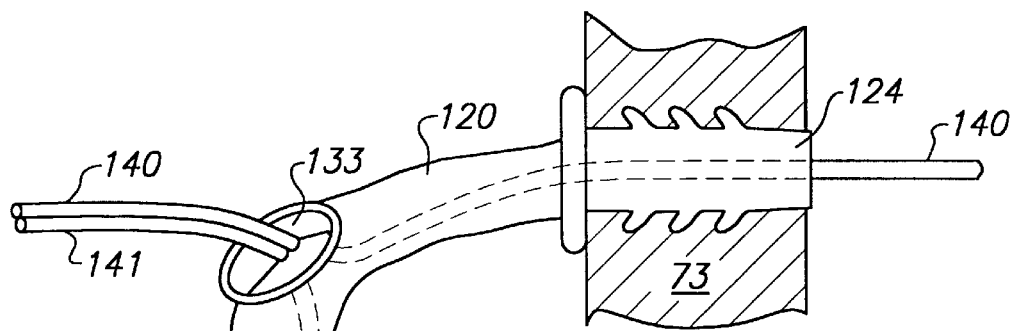

Conduit 120, pusher member 143 and exterior sheath are then advanced along guidewire 140 until the distal end of exterior sheath 144 abuts against the right atrial septum adjacent the transeptal passageway. Pusher member 143 is advanced within exterior sheath 144 to drive tubular member 124 into the transeptal passageway. The plurality of barbs or ribs 126 thereby engage septal myocardium 73, while the distal face of flange 125 abuts against the right atrial endocardium, as shown in FIG. 11B. Exterior sheath 144 and pusher member 143 are withdrawn along guidewire 140, leaving the guidewires 140 and 141 in place. When pusher member 143 is withdrawn, conduit 120 and fitting 128 are deployed, with guidewire 141 already extending from the distal end of fitting 128. Guidewire 140 is then withdrawn.

Figure 12:
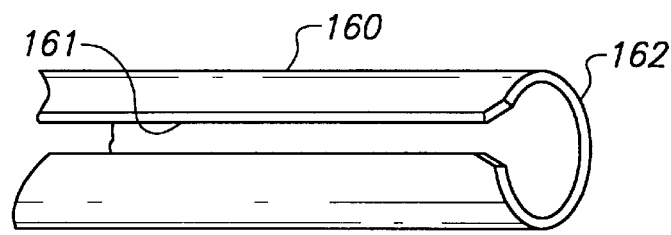
FIG. 12 is a partial perspective of a catheter for implanting a second end of the conduit of the present invention.

Referring now to FIG. 12, catheter 160 having slot 161 in its distal end is employed as will now be described. After deployment of conduit 120 and fitting 128 from within pusher member 143, guidewire 141 is manipulated so that-it enters the coronary sinus through the coronary ostium. Catheter 160 is then advanced along guidewire 141. Slot 161 in catheter 160 is sized to permit conduit 120 to slide within catheter 160 through slot 161, so that distal end face 162 abuts directly against the proximal face of flange 130. Once catheter 160 contacts flange 130 of fitting 128, catheter 160 is further advanced along guidewire 141 to drive the tapered end of fitting 128 through the coronary ostium and into engagement with the interior wall of the coronary sinus. Catheter 160 and guidewire 141 are then withdrawn, completing the implantation of conduit 120.

As will of course be apparent to one of skill in the art, other methods for transluminally implanting conduit 120 may occur to one of skill in the art. For example, instead of catheter 160, the grasping teeth of a myocardial biopsy catheter may be used to grasp fitting 128 and steer the fitting into engagement with the coronary ostium. Additionally, a second biopsy catheter could be brought into the right atrium via the right femoral artery, if desired, to assist in implantation of either or both ends of conduit 120.

While preferred illustrative embodiments of the invention are described above, it will be obvious to one skilled in the art that various changes and modifications may be made therein without departing from the invention and the appended claims are intended to cover all such changes and modifications which fall within the true spirit and scope of the invention.

What is claimed is:

1. Apparatus for use in treating ischemic heart disease by providing long-term retrograde transvenous myocardial perfusion, the apparatus comprising:

a conduit adapted to be disposed between a patient's left ventricle and the patient's coronary sinus, so that blood flows through the conduit from the left ventricle to the coronary sinus during cardiac systole;

means for partially occluding the patient's coronary ostium; and a valve for limiting a peak pressure attained within the coronary sinus by venting blood from the conduit into the patient's right atrium when the pressure attained within the coronary sinus exceeds a predetermined value.

2. The apparatus as defined in claim 1 further comprising:

a cutting instrument adapted for insertion into the coronary sinus via the coronary ostium, the cutting instrument boring through a wall of the coronary sinus, through the patient's epicardium, myocardium and endocardium to create a passageway between the left ventricle and the coronary sinus within which the conduit is implanted.

3. The apparatus as defined in claim 1 wherein the conduit comprises:

a tubular member having a central bore, and exterior surface, and a plurality of engagement means located on the exterior surface.

4. The apparatus as defined in claim 3 wherein the tubular member further comprises a one-way valve that prevents backflow of blood from the coronary sinus to the left ventricle.

5. The apparatus as defined in claim 1 wherein the valve is disposed within a bore of the means for partially occluding the coronary ostium, the valve opening when the pressure exceeds the predetermined value.

6. The apparatus as defined in claim 1 wherein the conduit comprises:

a tubular member having a first end, a second end, and a lumen extending therebetween, the tubular member comprising a flexible material, the means for partially occluding comprising the second end of the tubular member;

means for engaging the first end of the tubular member in a passageway extending from the right atrial endocardium and into the left ventricular septal endocardium; and means for engaging the second end of the device in the coronary ostium.

7. The apparatus as defined in claim 6 wherein the first and second ends of the conduit are adapted for transluminal implantation.

8. The apparatus as defined in claim 6 wherein the means for engaging comprises a plurality of ribs or barbs.

9. The apparatus as defined in claim 6 wherein the conduit further comprises a one-way valve that prevents backflow of blood from the coronary sinus to the left ventricle.

10. The apparatus as defined in claim 6 wherein the valve is disposed in the conduit.

11. A kit for use in treating ischemic heart disease by providing long-term retrograde transvenous myocardial perfusion, the kit comprising:

means for forming a passageway having first and second ends, the first end in fluid communication with a patient's left ventricle, the second end in fluid communication with the patient's coronary sinus, the passageway providing a lumen for blood flow from the left ventricle to the coronary sinus and extending from an interior surface of the coronary sinus into the left ventricle, the means for forming configured for percutaneous, transluminal insertion into the coronary sinus;

a plug adapted to be disposed in the patient's coronary ostium to partially occlude the coronary ostium.

12. The kit as defined in claim 11 wherein the plug further comprises a valve that limits a peak pressure attained within the coronary sinus by venting blood from the coronary sinus into the patient's right atrium when the pressure attained within the coronary sinus exceeds a predetermined value.

13. The kit as defined in claim 11 further comprising:

a delivery system adapted for percutaneous insertion into coronary ostium to deliver the plug.

14. The kit as defined in claim 11 further comprising:

a tubular member having a central bore, an exterior surface, and a plurality of engagement means located on the exterior surface, the tubular member configured for percutaneous, transluminal insertion in the passageway so that the plurality of engagement means engage a tissue surface within the passageway.

15. The kit as defined in claim 14 wherein the plurality of engagement means comprises a plurality of ribs or barbs.

16. The kit as defined in claim 14 wherein the tubular member further comprises a one-way valve that prevents backflow of blood from the coronary sinus to the left ventricle.

17. Apparatus for use in treating ischemic heart disease by providing long-term retrograde transvenous myocardial perfusion, the apparatus comprising:

a conduit having first and second ends and an intermediate portion located between the first and second ends, the first end adapted to be disposed in fluid communication with a patient's left ventricle, the second end adapted to be disposed in the coronary ostium in fluid communication with the patient's coronary sinus, the conduit providing a lumen for blood flow from the left ventricle to the coronary sinus during cardiac systole, a first region of the conduit near the first end adapted to be disposed in a passageway extending between the right atrial endocardium and the left ventricular septal endocardium, the intermediate portion extending into the right atrium;

a valve disposed in the intermediate portion to limit a peak pressure attained within the coronary sinus, the valve venting blood from the coronary sinus into the right atrium when the pressure attained within the coronary sinus exceeds a predetermined value.

18. The apparatus as defined in claim 17 further comprising:
   a cutting instrument adapted for percutaneous insertion into the right atrium to create a passageway extending from the right atrial endocardium and into the left ventricular septal endocardium.

19. The apparatus as defined in claim 17 wherein the conduit further comprises:
   a tubular member formed from a flexible material;
   means for engaging the first region in the passageway extending between the right atrial endocardium and the left ventricular septal endocardium; and
   means for engaging the second end within the coronary sinus through the coronary ostium.

20. The apparatus as defined in claim 19 wherein the means for engaging comprises a plurality of ribs or barbs.

21. The apparatus as defined in claim 17 wherein the conduit further comprises a one-way valve disposed within the lumen between the first end and the intermediate portion, the one-way valve preventing backflow of blood from the coronary sinus to the left ventricle.

22. The apparatus as defined in claim 17 wherein the conduit is adapted for percutaneous implantation.

* * * * *